(12) United States Patent
Chang

(10) Patent No.: US 7,304,848 B2
(45) Date of Patent: Dec. 4, 2007

(54) APPARATUS FOR PERFORMANCE TESTING OF HEAT DISSIPATING MODULES

(75) Inventor: Chun-Yi Chang, Tu-Cheng (TW)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 78 days.

(21) Appl. No.: 11/384,458

(22) Filed: Mar. 20, 2006

(65) Prior Publication Data

US 2007/0014091 A1    Jan. 18, 2007

(30) Foreign Application Priority Data

Jul. 15, 2005    (CN) .......................... 2005 1 0036035

(51) Int. Cl.
H05K 7/20    (2006.01)

(52) U.S. Cl. ...................... 361/701; 361/704; 361/715; 361/690; 361/692; 324/537; 324/760; 374/135; 374/141; 374/145; 165/67; 165/80.2; 165/80.3; 702/131

(58) Field of Classification Search ........ 361/690–697, 361/687, 700–703, 712–719; 702/113, 123, 702/130, 132, 133–136; 700/299, 300; 374/45, 374/52, 57, 100, 102, 152, 134, 141, 145; 165/80.2, 80.3, 80.4, 80.5, 104.32, 104.33, 165/104.34; 340/501, 584, 589; 324/537, 324/760; 73/865.6, 865.8
See application file for complete search history.

(56) References Cited

U.S. PATENT DOCUMENTS

| | | | | |
|---|---|---|---|---|
| 6,246,969 | B1 * | 6/2001 | Sinclair et al. | 702/113 |
| 6,277,701 | B1 * | 8/2001 | Noble | 438/359 |
| 6,418,393 | B1 * | 7/2002 | Lu et al. | 702/130 |
| 7,168,851 | B2 * | 1/2007 | Kim et al. | 374/44 |

FOREIGN PATENT DOCUMENTS

TW        M252065         12/2004

* cited by examiner

Primary Examiner—Michael Datskovskiy
(74) Attorney, Agent, or Firm—Jeffrey T. Knapp

(57) ABSTRACT

An apparatus (10) for performance testing of heat dissipating modules (19) includes an enclosure (11) configured for receiving the heat dissipating module therein, a vertically movable platform (13) for supporting the enclosure thereon, a boosting mechanism (18) configured for raising the vertically movable platform, and a force gage (12) having a force-sensing portion (121) configured for abutting against a top of the heat dissipating module. The enclosure includes a mounting base (110) having a plurality of mounting holes (1101) defined therein configured for mounting of heat dissipating modules with various sizes thereon. The present heat dissipating module testing apparatus can fit heat dissipating modules with various sizes. Thus saving both cost and time in testing.

12 Claims, 3 Drawing Sheets

APPARATUS FOR PERFORMANCE TESTING OF HEAT DISSIPATING MODULES

BACKGROUND OF THE INVENTION

1. Field of the Invention

The present invention relates to apparatuses for performance testing of heat dissipating modules and, more particularly, to an apparatus for performance testing of the heat transfer properties of heat dissipating modules with various sizes.

2. Discussion of the Related Art

Nowadays, with the rapid development of the technology of flat panel displays, notebook computers with high processing power are being made thinner and lighter. Thus the space available for components such as heat dissipating modules has been greatly reduced. However, high powered electronic devices like CPUs (Central Processing Units) produce large amounts of heat which must be dissipated. If heat generated by the CPU cannot be dissipated in a limited space, heat will be accumulated therein. The high temperature caused by this accumulating heat will adversely influence performance and reduce the service life of the products. Therefore, the designs of heat dissipating modules are important.

In a process of designing a heat dissipating module, testing is an important step. After a heat dissipating module is designed, the heat transfer properties of the heat dissipating module must be tested. However, before the testing step, a mounting base for mounting the heat dissipating module in the testing apparatus must be manufactured. Since different heat dissipating modules need different mounting bases, if positions of components of the heat dissipating module are changed, a new mounting base is needed to fix the heat dissipating module. Thus, much time and cost will be wasted in the testing whilst the bases are being manufactured.

What is needed, therefore, is a heat dissipating module testing apparatus for performance testing heat transfer property of heat dissipating modules which can be adjusted to fit various sizes.

SUMMARY OF THE INVENTION

A heat dissipating module testing apparatus for performance testing of a heat dissipating module according to one preferred embodiment includes an enclosure configured for receiving the heat dissipating module therein, a vertically movable platform for supporting the enclosure thereon, a boosting mechanism configured for raising the vertically movable platform, and a force gage having a force-sensing portion configured for abutting against a top of the heat dissipating module. The enclosure includes a mounting base having a plurality of mounting holes defined therein configured for mounting heat dissipating modules with various sizes thereon.

Compared with conventional heat dissipating module testing apparatus, the present heat dissipating module testing apparatus has following advantages. Because the mounting base has a plurality of mounting holes defined therein, the heat dissipating module testing apparatus can fit heat dissipating modules with various sizes without requiring a new base to be manufactured. Therefore, cost and time is saved in the testing step.

Other advantages and novel features will become more apparent from the following detailed description of the present heat dissipating module testing apparatus when taken in conjunction with the accompanying drawings.

BRIEF DESCRIPTION OF THE DRAWINGS

Many aspects of the present apparatus can be better understood with reference to the following drawings. The components in the drawings are not necessarily drawn to scale, the emphasis instead being placed upon clearly illustrating the principles of the present apparatus. Moreover, in the drawings, like reference numerals designate corresponding parts throughout the several views.

DETAILED DESCRIPTION OF PREFERRED EMBODIMENTS

Reference will now be made to the drawings to describe preferred embodiments of the present measurement apparatus for heat dissipating module, in detail.

Figure 1:
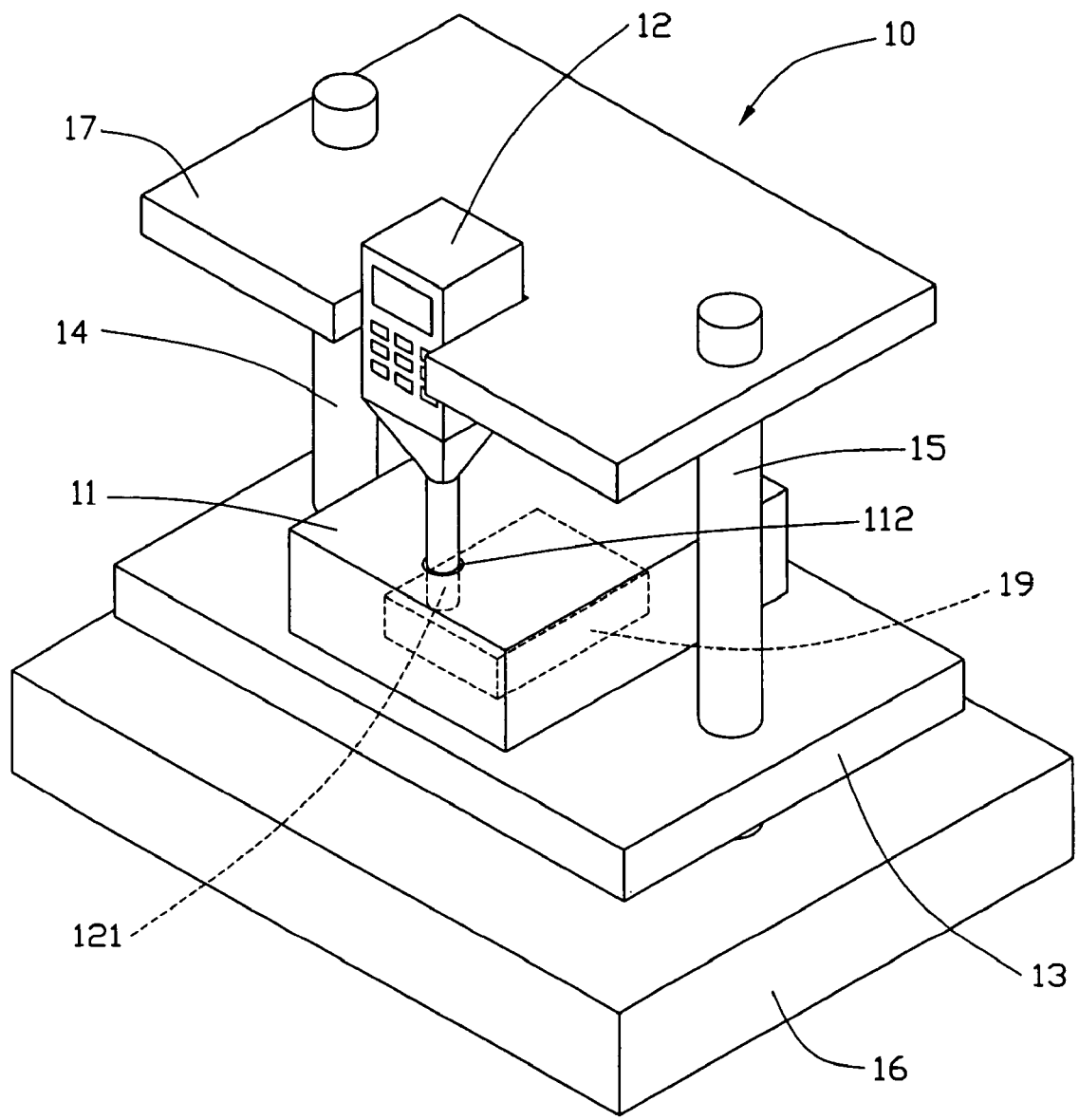
FIG. 1 is an isometric view of an apparatus for performance testing of heat dissipating modules with various sizes in accordance with a preferred embodiment.
Figure 2:
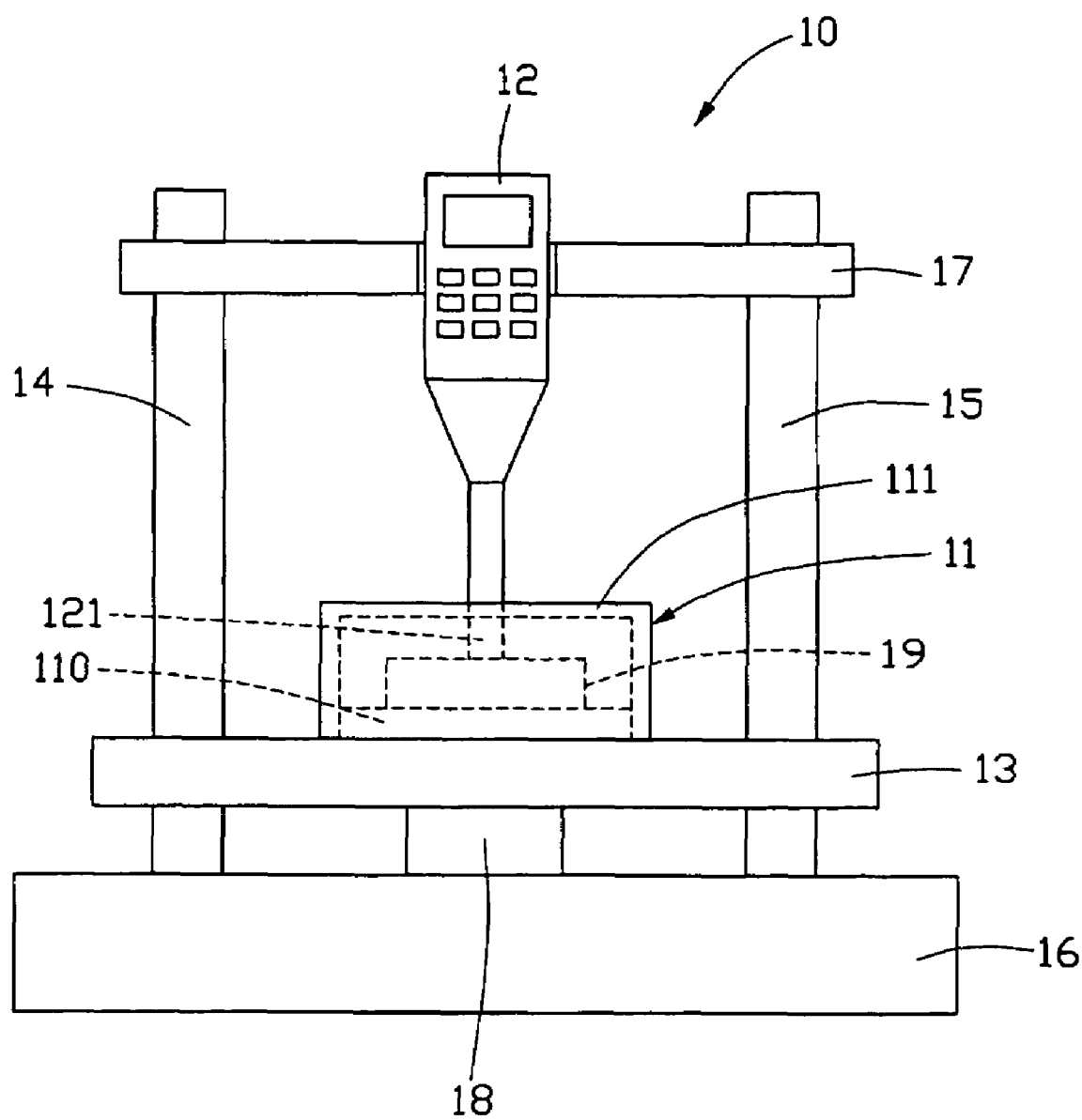
FIG. 2 is a schematic, side view of the apparatus of FIG. 1.

Referring to FIGS. 1 and 2, an apparatus 10 for performance testing of a heat dissipating module, in accordance with a preferred embodiment, is shown. The heat dissipating module testing apparatus 10 includes an enclosure 11, a vertically movable platform 13, a boosting mechanism 18 and a force gage 12. The enclosure 11 receives a heat dissipating module 19 therein. The vertically movable platform 13 is used to support the enclosure 11 thereon. The boosting mechanism 18 is utilized to raise the vertically movable platform 13. The force gage 12 has a force-sensing portion 121 configured for abutting against a top of the heat dissipating module 19.

The apparatus 10 further includes a base 16, at least two guiding posts 14, 15 extending from the base 16, and a stationary plate 17 disposed distally near the upper ends of the guiding posts 14, 15. The guiding posts 14, 15 are aligned in parallel with each other. The vertically movable platform 13 forms a plane aligned in parallel with that formed by the base 16 and can be moved along the guiding posts 14, 15. The force gage 12 is secured to the stationary plate 17.

The boosting mechanism 18 is interposed between the vertically movable platform 13 and the base 16. The boosting mechanism 18 is a hydraulic pressure boosting mechanism or a jacking screw boosting device which makes the vertically movable platform 13 move along the guiding posts 14, 15.

The enclosure 11 includes a mounting base 110 and a cover 111. The force-sensing portion 121 of the force gage 12 contacts with the top of the heat dissipating module 19 through a through hole 112 defined on the cover 111 of the enclosure 11, and inflicts a stress upon the heat dissipating module 19. Using the boosting mechanism 18 which raises the vertically movable platform 13, stress magnitude can be adjusted. This stress is then measured by the force gage 12.

The enclosure 11 is arranged on the vertically movable platform 13, and moves with the vertically movable platform 13.

Figure 3:
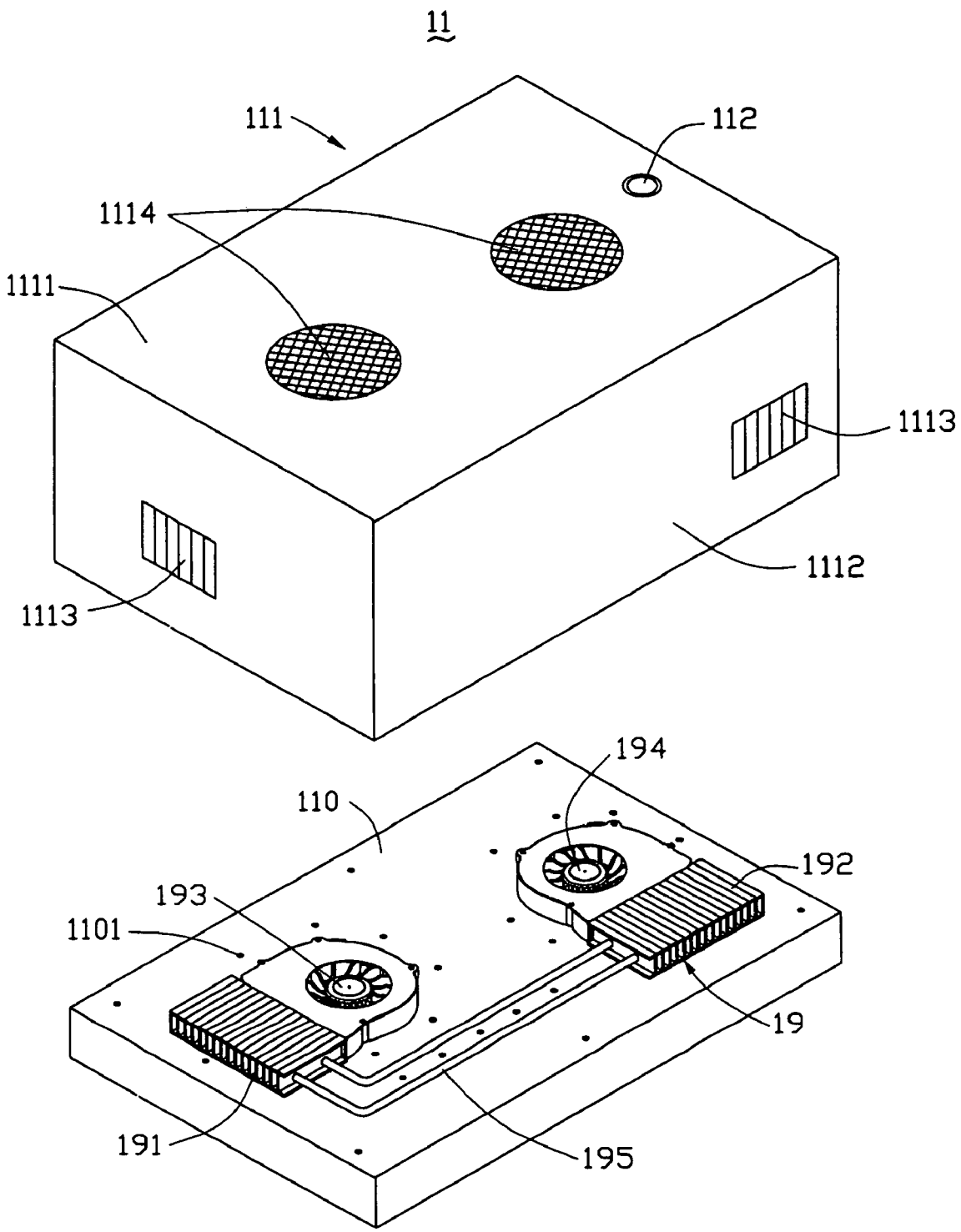
FIG. 3 is an exploded, isometric view of an enclosure of FIG. 1.

Referring to FIG. 3, the enclosure 11 of FIGS. 1 and 2 is shown. The enclosure 11 includes a mounting base 110 and a cover 111. The mounting base 110 and the cover 111 are made of a material with poor heat conductivity and good thermal properties, such as phenolic resin. A plurality of mounting holes 1101 are regularly distributed in the mounting base 17 for mounting all components of the heat dissipating module 19. The mounting holes 1101 can be of various shapes and various types, such as screw holes.

The enclosure 11 further includes a heat source (not shown) on the mounting base 110. The heater band imitates the heat production of for example a CPU of a notebook computer. In this embodiment, the heat source is a heater band with high thermal resistance which can adjust the heat generated by the heat source.

The heat dissipating module 19 includes at least one heat sink 191 and at least one fan 193. The heat sink 191 and the fan 193 are fixed on the mounting base 110 by screws inserting the mounting holes 1101 and the heat sink 191 is placed adjacent to the fan 193.

The heat dissipating module 19 may be various combinations of different heat conductive components under various needs. In this case, the heat dissipating module 19 includes two heat sinks 191, 192, two fans 193, 194, and a heat pipe 195. The heat sinks 191, 192 are each positioned adjacent to the fans 193, 194 respectively. The heat sinks 191, 192 are thermally connected through the heat pipe 195.

The cover 111 is assembled with a top plate 1111 and a plurality of side plates 1112. The top plate 1111 is perpendicular with the side plates 1112. The top plate 181 is fixed on the top of the side plates 183 and is detachable from the cover 111. The side plates 1112 are also detachable form the cover 111. When testing, the cover 111 covers the mounting base 110, and provides an inner space imitating that of a notebook computer.

Furthermore, the through hole 112 is defined in the top plate 1111. When testing, the force-sensing portion 121 of the force gage 12 inflicts a stress upon the heat sink 192 through the through hole 112. Thereby, heat conduction efficiency of the heat sink 192 is improved.

A ventilation entrance 1114 is arranged on the top plate 1111 and in a position corresponding to that of the fan 193. Cold air flows into the enclosure 11 through the ventilation entrance 1114, and cools the heat dissipating module 19. In this case, since the heat dissipating module 19 includes two fans 193, 194, two ventilation entrances 185 are needed.

A ventilation exit 1113 is arranged on the side plate 183 for heat dissipating through moving hot air, and is positioned corresponding to the heat sink 191. In this case, since the heat dissipating module 19 includes two heat sinks 191, 192, two ventilation exits 1113 are needed.

In this embodiment, the apparatus 10 tests heat transfer efficiency by imitating the inner conditions of the notebook computer. When testing, the heat dissipating module 19 is fixed on the mounting base 110, thermocouples are arranged at different important positions for measuring temperature. Then the cover 111 is covered, and the enclosure 11 is set on the vertically movable platform 13. The force-sensing portion 121 of the force gage 12 exerts a stress upon the heat dissipating module 19, and adjusts the stress. The heat source starts to work. Then the temperatures of various different important positions are measured by thermocouples. In this way heat transfer efficiency of the heat dissipating module 19 can be tested.

Compared with a conventional heat dissipating module testing apparatus, the present apparatus 10 has following advantages.

Firstly, the apparatus 10 uses the mounting base 110 with a plurality of mounting holes 1101 configured for mounting heat dissipating modules with various sizes thereon. The components of the heat dissipating modules 19, such as heat sinks, fans, etc, can be fixed on the mounting base 110 by screws. That is, there is no need to manufacture different mounting bases for fixing different heat dissipating modules. Therefore, the cost and time of the testing is greatly reduced.

Secondly, the apparatus 10 uses the cover 111 to contain the hot elements of the machine. Thus, the effect on environmental conditions is reduced.

Thirdly, the cover 111 is assembled with the top plate 1111 and the plurality of side plates 1112, So, when the components of the heat dissipating module 19 are changed, only the top plate 1111 or the side plate 1112 need to be removed to gain access to the heat dissipating module 19. Therefore, it can be seen that this construction saves both time and money.

It is to be understood that the above-described embodiment is intended to illustrate rather than limit the invention. Variations may be made to the embodiment without departing from the spirit of the invention as claimed. The above-described embodiments are intended to illustrate the scope of the invention and not restrict the scope of the invention.

What is claimed is:

1. An apparatus for performance testing of heat dissipating modules with various sizes, comprising:
    an enclosure configured for receiving the heat dissipating module therein, the enclosure including a mounting base having a plurality of mounting holes defined therein configured for mounting heat dissipating modules with various sizes thereon;
    a vertically movable platform for supporting the enclosure thereon;
    a boosting mechanism configured for raising the vertically movable platform; and
    a force gage having a force-sensing portion configured for abutting against a top of the heat dissipating module.

2. The apparatus as claimed in claim 1, further comprising a base, at least two guiding posts extending from the base, and a stationary plate disposed distally of the guiding posts, the vertically movable platform being movable along the guiding posts, the force gage being secured to the stationary plate.

3. The apparatus as claimed in claim 1, wherein the enclosure includes a cover defining a through hole for extension of the force-sensing portion therethrough.

4. The apparatus as claimed in claim 2, wherein the boosting mechanism is interposed between the vertically movable platform and the base.

5. The apparatus as claimed in claim 1, wherein the enclosure further comprises a heat source arranged on the mounting base.

6. The apparatus as claimed in claim 5, wherein the cover comprises a top plate and a plurality of side plates, at least one of which is detachable from the cover.

7. The apparatus as claimed in claim 6, wherein the top plate is detachable from the cover.

8. The apparatus as claimed in claim 6, wherein each of the plurality of side plates is detachable from the cover.

9. The apparatus as claimed in claim 6, wherein the cover defines at least one ventilation entrance in the top plate, and at least one ventilation exit in the side plates.

10. The apparatus as claimed in claim 1, wherein the mounting base and the cover are made from a material with poor heat conductivity and good thermal properties.

11. The apparatus as claimed in claim 10, wherein the mounting base and the cover are made from phenolic resin.

12. The apparatus as claimed in claim 1, wherein the boosting mechanism is one of a hydraulic pressure boosting device and a jacking screw boosting device.

* * * * *